(12) United States Patent
Wilkinson et al.

(10) Patent No.: US 6,350,254 B1
(45) Date of Patent: Feb. 26, 2002

(54) MEDICAL DEVICE FOR FLUID COLLECTION AND METHOD TO FILL MULTIPLE SPECIMEN TUBES

(75) Inventors: Bradley M. Wilkinson, North Haledon; Robert S. Golabek, Jr., Towaco, both of NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/369,999

(22) Filed: Aug. 6, 1999

(51) Int. Cl.$^7$ .................................................. A61M 1/00
(52) U.S. Cl. ........................ 604/326; 600/574; 600/576; 222/165
(58) Field of Search ................................. 604/317, 322, 604/326, 327, 329, 346, 347, 349; 600/574–576; 222/164, 165, 577, 584; 248/133, 140

(56) References Cited

U.S. PATENT DOCUMENTS

| | | | |
|---|---|---|---|
| 3,750,647 A | 8/1973 | Gleason et al. | 128/2 F |
| 4,106,490 A | 8/1978 | Spilman et al. | 128/2 F |
| 4,116,066 A | 9/1978 | Mehl et al. | 73/421 R |
| 4,121,306 A | 10/1978 | Bringman et al. | 4/144.2 |
| 4,258,032 A | 3/1981 | Mehl | 424/148 |
| 4,300,404 A | 11/1981 | Mehl et al. | 73/863.52 |
| 4,335,730 A | 6/1982 | Griffin | 128/760 |
| 4,393,881 A * | 7/1983 | Shah | 128/760 |
| 4,492,258 A * | 1/1985 | Lichtenstein | 141/1 |
| 4,761,379 A | 8/1988 | Williams et al. | 435/296 |
| 4,769,215 A | 9/1988 | Ehrenkranz | 422/58 |
| 4,895,167 A * | 1/1990 | Guala | 128/760 |
| 5,069,878 A | 12/1991 | Ehrenkranz | 422/61 |
| 5,147,342 A | 9/1992 | Kane et al. | 604/356 |
| 5,251,639 A | 10/1993 | Rentsch | 128/761 |
| 5,422,076 A | 6/1995 | Jones | 422/102 |
| 5,569,225 A | 10/1996 | Fleury | 604/323 |
| 5,797,855 A | 8/1998 | Hazard et al. | 600/513 |
| 5,849,505 A | 12/1998 | Guirguis | 435/7.2 |
| 5,893,176 A | 4/1999 | Magiera et al. | 4/144.4 |
| 5,894,607 A | 4/1999 | Van Den Burg | 4/144.2 |
| 5,894,608 A | 4/1999 | Birbara | 4/144.3 |
| 5,897,840 A | 4/1999 | Owens, Jr. et al. | 422/102 |

* cited by examiner

Primary Examiner—John G. Weiss
Assistant Examiner—Jamisue Webb
(74) Attorney, Agent, or Firm—Keith J. McWha; Nanette S. Thomas (57) ABSTRACT

A medical device for fluid collection and method to fill multiple specimen tubes is disclosed. The device is designed to collect and transfer a specimen into a non-evacuated tube through an integrated open port. The device has no cannulas, either blunt or sharp, and therefore provides safety from skin puncture. The device has a non-evacuated test tube attached to the integrated open port. The tube is attached to the open port by a luer fitting in the tube's cap which is pressed into a receptacle detail on the device. A finger pad is held during collection of the specimen. The finger pad allows collection without the risk of contaminating the inside of the container. The container also contains a horizontal support platform which allows the device to be placed on a flat surface with or without the test tube attached without tipping over. The specimen is transferred into the non-evacuated tube by holding a vertical platform which is attached to the horizontal support platform and tilting the device so the liquid specimen rolls up an inclined top surface towards a transfer port hole. There is instant visual feedback of the transfer of the specimen. This type of transfer allows transfer of the specimen with total control of the volume transferred into the test tube. It also reduces the risk of contacting or contaminating the specimen. Gravity allows the specimen to transfer into the tube and transfer will stop when the device is tilted back into its original flat position. The test tube is then pulled off the container and a second tube may be filled at that time. The device is then discarded for proper disposal. Further specimen transfer from the device when the device is on a flat surface is not a risk since the portal hole is at the highest gravitational point on the inside top surface.

4 Claims, 7 Drawing Sheets

MEDICAL DEVICE FOR FLUID COLLECTION AND METHOD TO FILL MULTIPLE SPECIMEN TUBES

FIELD OF THE INVENTION

The invention relates generally to an apparatus and method for collecting and transferring biological fluids. More particularly, the present invention relates to an apparatus and method for collecting and transferring a urine specimen in conjunction with a collection tube.

DESCRIPTION OF PRIOR ART

Biological fluids are collected periodically for laboratory analysis. Laboratory equipment that performs the analysis may only accept biological fluids stored in a test tube. However, a test tube is too small for the convenient collection of many biological fluids, such as urine. As a result, specimens often are collected in a fairly large container with a widely open top. After collection of the fluid in the container, the container is delivered to a medical technician. The technician then transfers a portion of the fluid to a test tube that can be sealed and transported to a laboratory for analysis. The transfer of biological fluid from the collection container to the test tube is an unpleasant task that creates the risk of contaminating the specimen or exposing the medical technician to potentially harmful pathogens in the specimen.

Some biological fluids such as blood are collected with assemblies that include a vacuum tube and a double-ended needle cannula. One end of the needle cannula is placed in communication with the biological fluid. The opposite end of the needle cannula is urged through a vacuum seal into the vacuum tube. Low pressure within the vacuum tube generates a flow of the bodily fluid through the needle cannula and into the tube. Such vacuum tubes are very convenient and efficient for collecting blood samples. However, for urine specimen collection, vacuum tubes are not very useful because vacuum tubes only have a limited shelf life due to a gradual migration of gas molecules through the walls of the tube. Additionally, sharps or pointed cannula require careful shielding to avoid potential skin punctures.

In urine collection, some prior art collection containers have a test tube that is attached. In these prior art devices, a portion of the urine specimen in the container is automatically transferred to the test tube. The test tube then may be separated from the container, sealed and shipped to a laboratory for analysis. However, these prior art assemblies can lead to leakage during the initial collection of the specimen or after the separation of the test tube from the collection container. Additionally, control of the volume of the specimen in the test tube may vary from sample to sample. A means for controlling the volume in each specimen sample taken is needed to assure accurate results in the subsequent laboratory analysis. Also, the use of a non-sharp or blunt fittings in the transfer of the specimen from the collection container to the test tube is preferred to avoid potential skin puncturing of the medical technician. Finally, a collection container designed to avoid contact with the user to prevent contamination of the specimen is desired. Prior art assemblies of collection containers can come into contact with the user's hands during collection which contaminate the specimen in the collection container. Finally, there is a need for a collection container to use a non-evacuated vacuum tube to avoid the potential limited shelf life of the vacuum tube.

SUMMARY OF THE INVENTION

The present invention alleviates in great part the drawbacks associated with prior art fluid collection devices. Provided is a device for precise and controllable transfer of a specimen from a collection container to a test tube. The present invention preserves non-contamination during collection and transfer between the collection container and the test tube.

The invention is directed to a medical device for fluid collection with a test tube. The medical device has a container having a curved bottom, an open top defining a plane, and a plurality of side walls extending from the bottom to the top. The bottom has a top surface and a bottom surface. The top surface is sloped with respect to the plane. The top surface also has a hole located at the highest gravitational point relative to the plane.

The device further includes an open port protruding outwardly from the bottom surface. The open port is in fluid communication with the hole. The port has an attachment portion for releasably locking the test tube onto the port and enabling the test tube filling only when the container is tilted.

The medical device further comprises a support platform attached to at least one of the side walls for flat surface support. The platform is vertically attached to at least one of the side walls. Also, a horizontal support platform is centrally attached to the vertical support platform and at least one of the side walls.

In addition, the medical device further comprises a finger pad horizontally mounted onto the side walls adjacent to the hole and opposite the vertical and horizontal support platforms. The finger pad has a curved portion vertically and distally mounted to the finger pad for slip resistant holding.

The container and open port are made of a single unitary structure. However, they do not have to be so constructed and may be separate components.

The side walls further include a depression located adjacent to the open port for releasably locking the test tube during collection. The attachment portion of the open port is an interior luer fitting. The open port further includes a segmented annular sheath protruding from the bottom. One of the side walls further defines a recessed receptacle detail distal from the open port. The sheath and the receptacle detail are for providing additional releasable locking support to the test tube.

The side walls further define a depression adjacent to the hole on the top surface of the device. The depression is to mate with a connector which releasably locks the test tube during collection. The side walls further include a flat adjacent to the open port for supporting the flip lid during collection. The test tube further includes a closed bottom, a top and cylindrical side walls extending from the closed bottom to the top. A cap is disposed on the top of the test tube. The cap has a male luer fitting protruding distally from the cap. The open port that protrudes out from the bottom surface of the device has an interior luer fitting for releasably locking with the male fitting of the cap. This fitting enables the test tube to fill only when the container is tilted. Thus, even though the test tube is attached to the container, transfer of the fluid into the test tube does not automatically commence. The container must be tilted for transfer of the fluid to begin.

The cap further includes a hinge and a flip lid hingedly connected to the cap. The flip lid includes the connector that releasably locks into the depression to secure the test tube during collection. The open port further includes a segmented annular sheath. One of the side walls defines a recessed receptacle detail. The annular sheath protrudes from the bottom surface creating a space such that the hinge of the cap releasably locks into the space and the flip lid releasably locks into the receptacle detail.

The method for filling multiple test tubes used in the medical device comprises the steps of providing the container having a curved bottom, an open top, and a plurality of side walls, the bottom having a sloped top surface and a bottom surface. The top surface defining a hole located at the highest gravitational point on the top surface. The container further including an open port protruding out from the bottom surface and in fluid communication with the hole. A finger pad is mounted horizontally on the side walls adjacent to the hole and opposite a vertical and horizontal support platform. The support platforms are attached to the side walls for flat surface support. The next step is attaching the test tube to the open port. After the attachment step, the fluid is collected in the container. Contamination of the fluid is prevented by holding the finger pad. Next, the container is held by the vertical support platform, then, the container is tilted toward the hole to fill the test tube through the open port. The test tube is removed by placing the horizontal support platform of the container on a flat surface and pulling the test tube out of the open port. Finally, the test tube on the open port is replaced with another test tube and the container is tilted by the vertical platform toward the hole to fill the other test tube. In this method, the step of attaching the test tube to the open port is accomplished by an attachment portion, a segmented annular sheath, a depression and a recessed receptacle detail all included on the container.

BRIEF DESCRIPTION OF THE DRAWINGS

The invention is now described in greater detail by way of reference to the following drawings, wherein.

DETAILED DESCRIPTION OF THE INVENTION

While this invention is satisfied by embodiments in many different forms, there is shown in the drawings and herein described in detail preferred embodiments of the invention with the understanding that the present disclosure is considered exemplary of the principles of the invention and is not intended to limit the invention to the embodiments illustrated. The scope of the invention is measured by the appended claims and their equivalents. Referring to the drawings, FIGS. 1–9 depict a medical device 8. Device 8 includes a medical container 10 having a curved bottom 14, and open top 20 defining a plane "A" and a plurality of side walls 22 extending from bottom 14 to top 20. Bottom 14 has a top surface 24 and a bottom surface 30. Top surface 24 is sloped with respect to plane "A". Top surface 24 also defines a hole 32 located at a point 34 that is the highest gravitational point on top surface 24 relative to plane "A".

Figure 1:
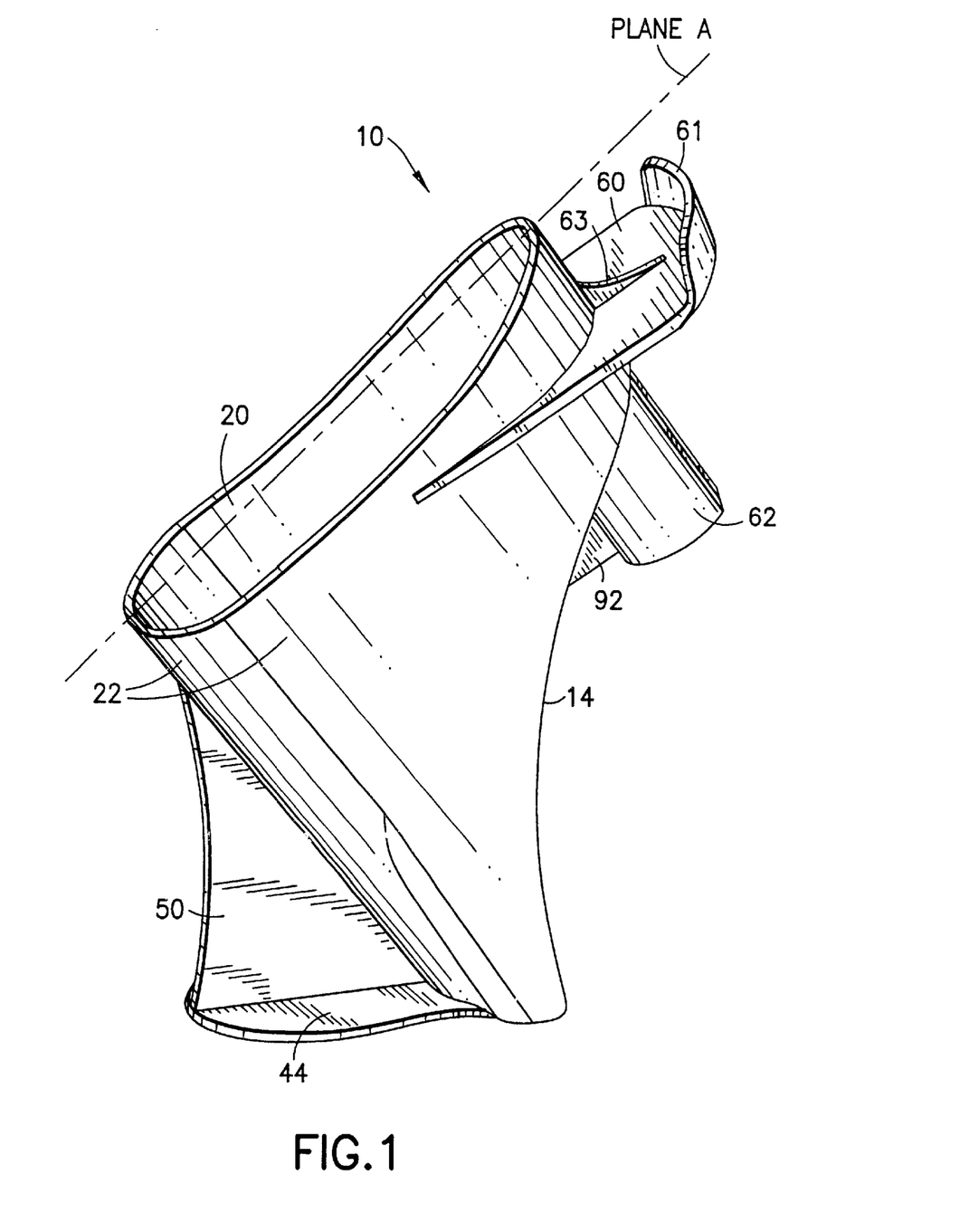
FIG. 1 is a perspective view of the medical device for fluid collection of the present invention.
Figure 2:
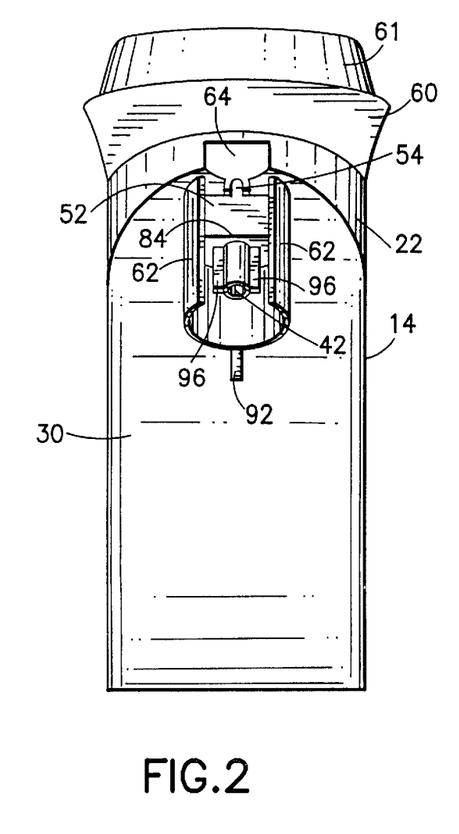
FIG. 2 shows a front view of the device in FIG. 1.
Figure 3:
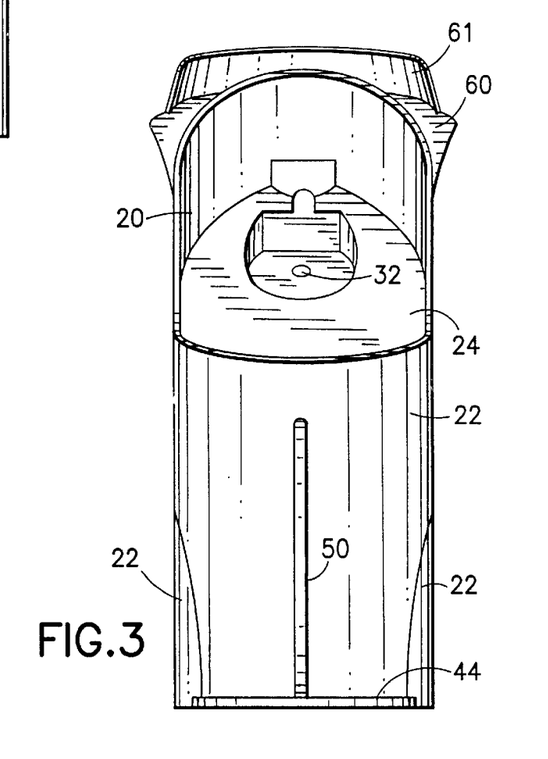
FIG. 3 shows a back view of the device in FIG. 1.
Figure 4:
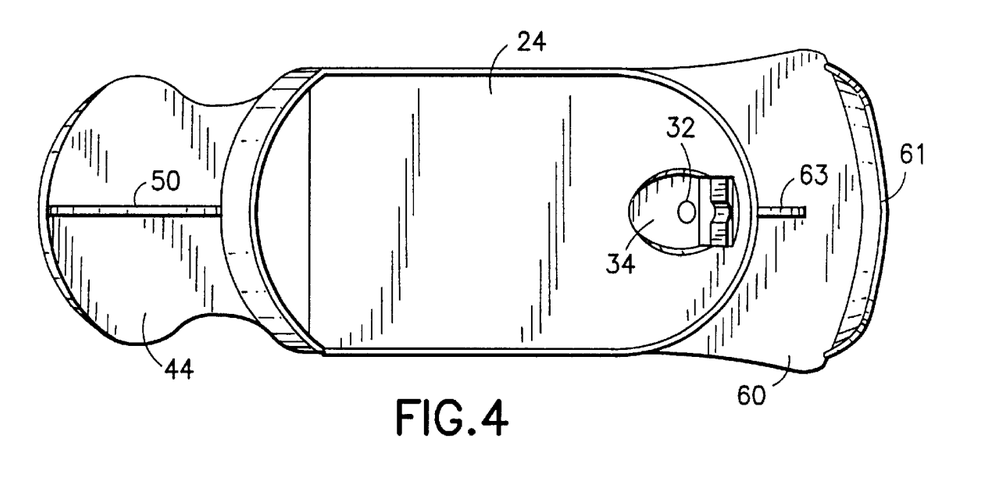
FIG. 4 shows a top view of the device in FIG. 1 relative to plane A, in FIG. 1.
Figure 5:
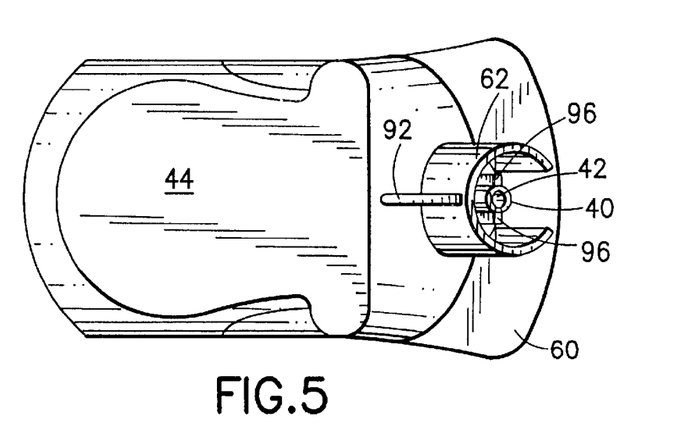
FIG. 5 illustrates a bottom view of the device in FIG. 1.

As shown in FIGS. 1 and 2, medical device 8 further includes an open port 40. Open port 40 protrudes outwardly from bottom surface 30. Open port 40 is in fluid communication with hole 32.

Port 40 is further characterized by having an attachment portion 42 for releasably locking a test tube 12 into port 40 and enabling test tube filling only when container 8 is tilted. Thus, even though test tube 12 is attached to container 10, transfer of fluid does not commence automatically. Container 10 must be tilted in order for fluid transfer to commence. Preferably, attachment portion 42 is an interior luer fitting. The luer fitting can be a luer slip or a luer lock, but is preferably a luer slip fitting.

A vertical support platform 50 is attached to at least one of the side walls 22 for flat surface support. Device 8 further comprises a horizontal support platform 44 centrally attached to vertical support platform 50 and at least one of the side walls 22. Horizontal platform 44 purpose is to give additional stability and flat surface support to device 8. However, platform 44 does not have to be attached to device 8 in which case vertical platform 50 would give flat surface support.

Device 8 further comprises a finger pad 60 horizontally mounted on side wall 22 adjacent to hole 32 and opposite vertical support platform 50 and horizontal support platform 44. The function of finger pad 60 is for holding the container 10. Finger pad 60 is further characterized by having a curved portion 61 vertically and distally mounted to pad 60. Curved portion 61 is for providing slip resistant holding of container 10. As shown in FIG. 1, a pad support rib 63 is centrally attached to pad 60 to provide rigidity to pad 60.

Preferably, container 10 and open port 40 are a single unitary structure. However, open port 40 could be a separate component attached to container 10. Attachment methods are well known to those skilled in the art. Such attachment methods would include snap fitting, ultrasonic welding, heat welding and adhesive bonding.

Figure 6:
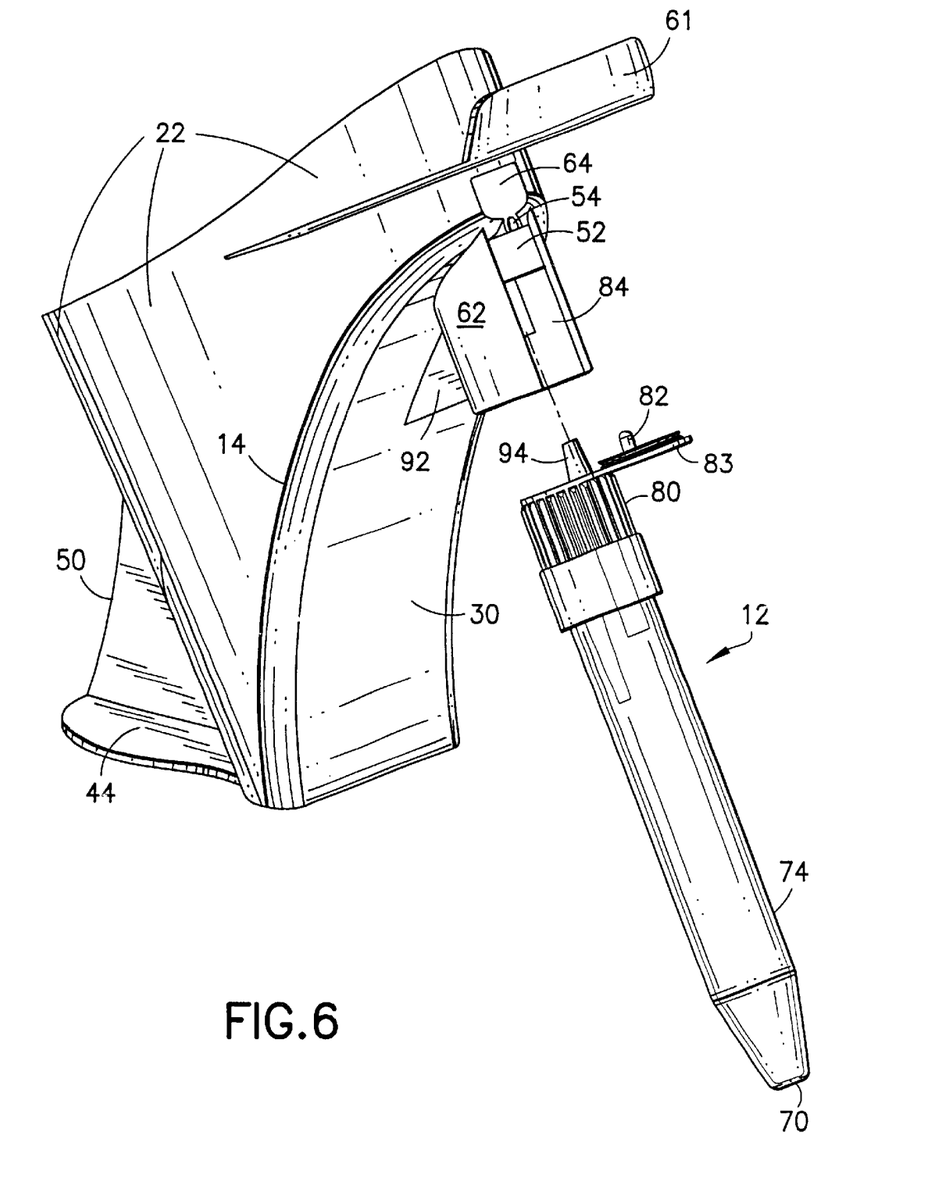
FIG. 6 is an exploded perspective view of the medical device in FIG. 1 in conjunction with a test tube.
Figure 7:
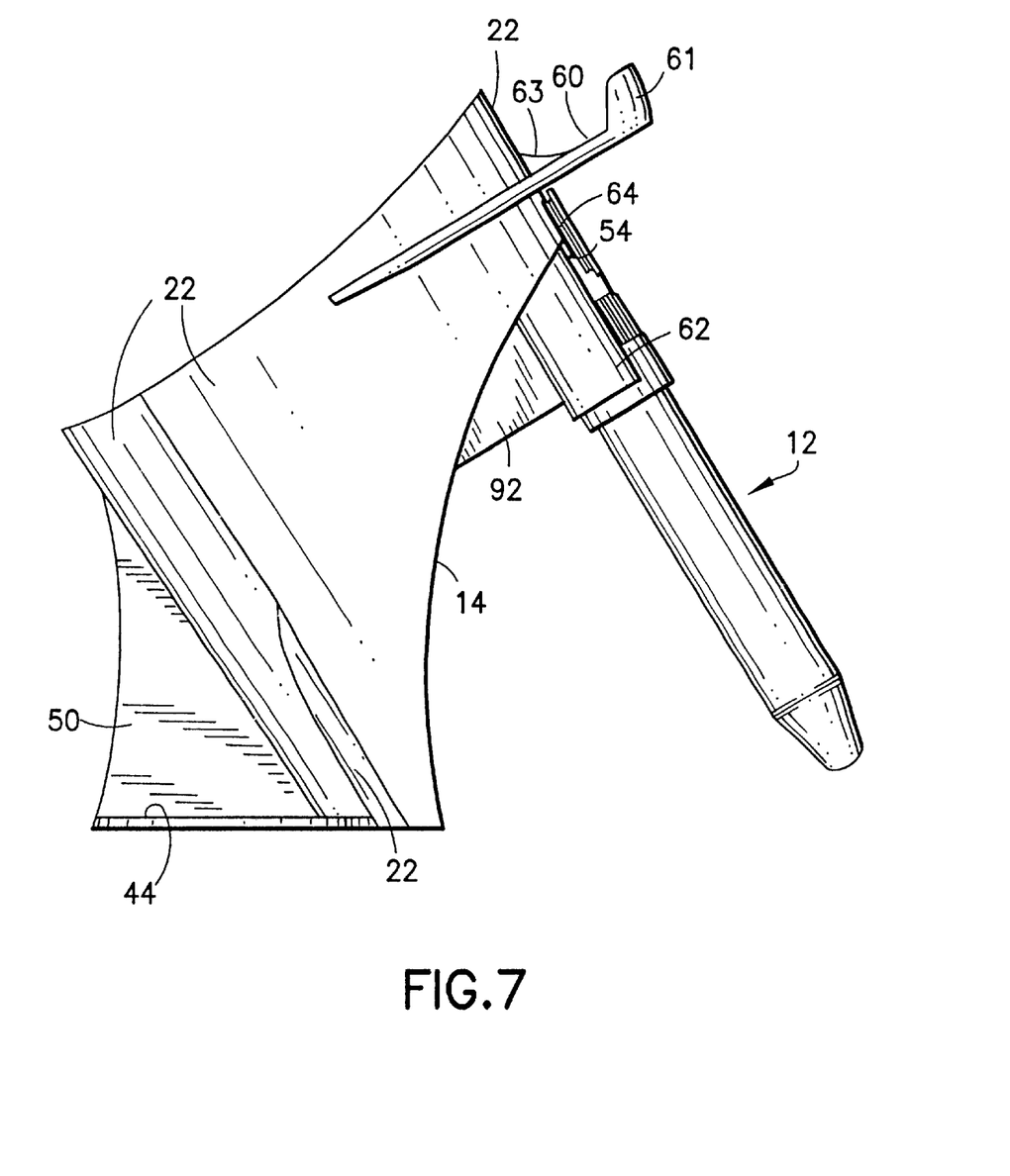
FIG. 7 is an assembled side view of FIG. 6.
Figures 8, 8A:
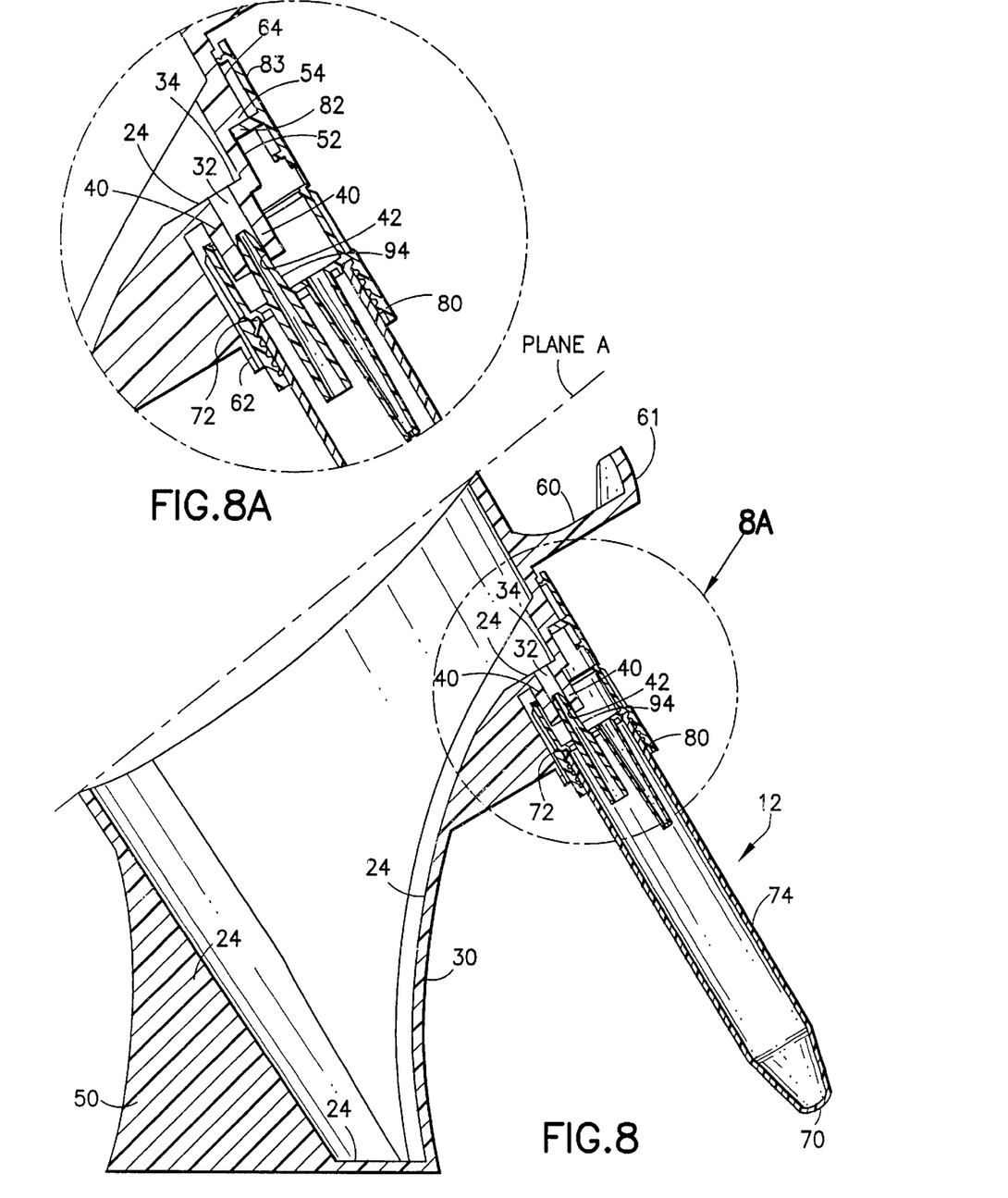
FIG. 8 is a cross-sectional view of FIG. 7.
FIG. 8a is an enlarged view of FIG. 8.
Figure 9:
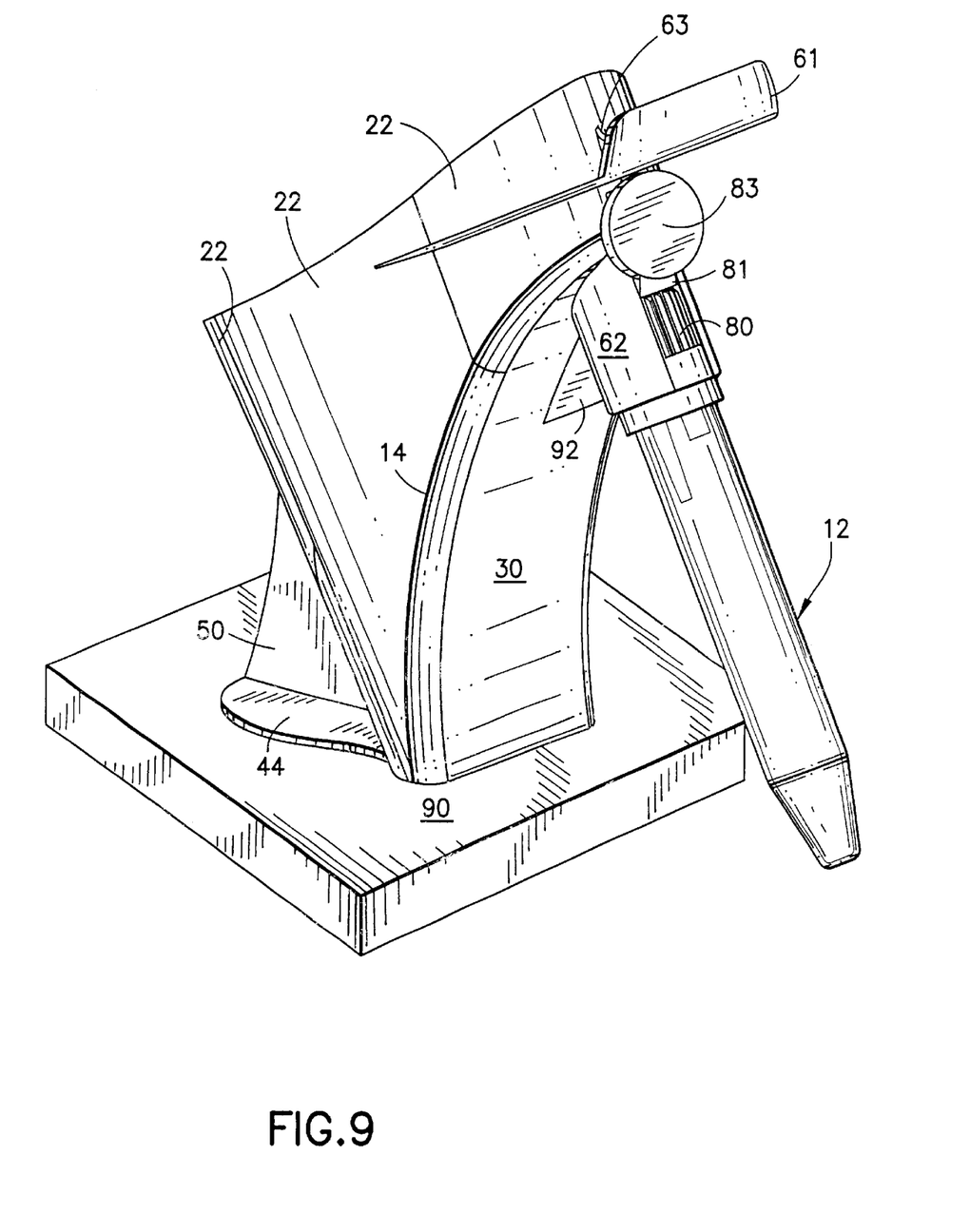
FIG. 9 is an assembled perspective view of FIG. 6.

Side walls 22 are further characterized by including a depression 54 located adjacent to open port 40 for releasably locking test tube 12 during collection. Open port 40 further includes a segmented annular sheath 62 protruding from bottom 30. One of said side walls 22 further defines a recessed receptacle detail 64 distal from open port 40. Sheath 62 and receptacle detail 64 provide additional releasable locking support to test tube 12. A support rib 92 attaches sheath 62 to bottom 30 as shown in FIG. 6.

Test tube 12 is characterized by having a closed bottom 70, a top 72 and a plurality of cylindrical side walls 74 extending from closed bottom 70 to top 72. Test tube 12 further includes a cap 80 disposed on top 72. Cap 80 is characterized by having a male luer fitting 94 protruding distally from cap 80. Male luer fitting 94 is releasably locked with attachment portion 42 of open port 40 for enabling test tube 12 to fill only when container 10 is tilted. Male luer fitting 94 is preferably a tapered plastic fitting. Thus, no cannula, neither blunt nor sharp is used to connect test tube 12 to container 10.

Cap 80 is further characterized by having a hinge 81 and a flip lid 83. Flip lid 83 is hingedly connected to cap 80 by hinge 81. Flip lid 83 further includes a connector 82 protruding distally from flip lid 83. The function of connector 82 is for releasably locking into depression 54 of side walls 22 to releasably secure test tube 12 during collection. Thus, container 10 has four structures for attaching test tube 12. These structures are attachment portion 42, annular sheath 62, recessed receptacle detail 64, and depression 54. By container 10 having four structures of attachment, secure attachment is enhanced during the tilting and transfer of fluid steps. Attachment portion 42 releasably attaches with male luer fitting 94.

Annular sheath 62 is further characterized by creating a space 84 such that hinge 81 releasably locks into space 84 when flip lid 83 releasably locks into recessed receptacle detail 64 and connector 82 releasably locks into depression 54. Side walls 22 are further characterized by including a flat surface 52, as shown in FIG. 2, adjacent to open port 40 for supporting flip lid 83 during collection.

During sample collection, male luer fitting 94 is inserted into attachment portion 42 of open port 40. Thereby, tube 12 is in fluid communication with container 10. However, no fluid transfer commences at this point. Open port 40 further includes port support ribs 96 to resist deformation and support open port 40 thereby maintaining the shape of attachment portion 42 and resisting any leakage due to deformation of attachment portion 42. Connector 82 of flip lid 83 is releasably attached into depression 54 of container 10. Hinge 81 of cap 80 removably attaches into space 84 of segmented annular sheath 62. The edges of flip lid 83 releasably attaches into recessed receptacle detail 64. Now test tube 12 is fully secured to container 10. The fluid specimen is then collected in container 10. Contamination of the specimen is prevented by holding container 10 by finger pad 60. Curved portion 61 allows slip-resistant holding of finger pad 60. At this point, no fluid is transferred even though tube 12 is attached to container 10. Container 10 is then tilted toward hole 32 to fill test tube 12 through open port 40. After visual confirmation of the volume of specimen transferred into test tube 12, container 10 is then placed on horizontal support platform 44 on a flat surface 90. Test tube 12 is removed out of open port 40. No further transfer of the specimen from container 10 is allowed because of the curvature of curved bottom 14 and the slope of top surface 24, which leads to hole 32, prevents further transfer. Test tube 12 can be replaced with another test tube in open port 40 if multiple specimens are desired. The procedure of tilting container 10 is repeated to fill the other test tube as the specimen flows toward and through hole 32.

The present invention allows control over when and how much volume of specimen is transferred into test tube 12 by the tilting of container 10. In addition, test tube 12 is securely and releasably attached during sample collection to medical container 10 by a variety of components allowing secure transfer of fluid. These components include depression 54 attached into connector 82 of flip lid 83, hinge 81 of cap 80 removably attached into space 84 of segmented annular sheath 62, recessed receptacle detail 64 attached to the edges of flip lid 83 and male luer fitting 94 attached and in fluid communication with attachment portion 42. Thus, the present invention enables a specimen to be transferred to various volumes while providing safety from spills or leakage by manually controlling the volume in test tube 12 simply by tilting medical container 10.

What is claimed is:

1. A medical device for fluid collection with a test tube, comprising:
    a container having a curved bottom, an open top defining a plane, and a plurality of side walls extending from said bottom to said top, said bottom having a top surface and a bottom surface, said top surface sloped with respect to said plane, said top surface defining a hole;
    an open port protruding out from said bottom surface and in fluid communication with said hole, said port having an attachment portion for releasably locking the test tube into said port and enabling test tube filling only when the container is tilted, said open port further including a segmented annular sheath protruding from said bottom and said side walls further including a recessed receptacle detail distal from said open port, said sheath and said receptacle detail for providing additional releasable locking support to said test tube; wherein said side walls further defining a depression located adjacent to said open port for releasably locking the test tube during collection;
    a vertical support platform attached to at least one of said side walls for flat surface support; wherein said platform is vertically attached to at least one of said sidewalls; a horizontal support platform centrally attached to said vertical support platform and at least one of said side walls; and a finger pad horizontally mounted onto said side wall adjacent said hole and opposite said vertical and horizontal support platforms for holding said container, wherein said finger pad comprises a curved portion vertically and distally mounted thereto for slip resistant holding.

2. The device of claim 1, wherein said attachment portion of said open port is an interior luer fitting.

3. A medical device for fluid collection, comprising;
    a container having a curved bottom, an open top of said container defining a plane and a plurality of side walls extending form said bottom to said top of said container, said bottom having a top surface and a bottom surface, said top surface sloped with respect to said plane, said top surface defining a hole, wherein said side walls defining a depression adjacent to said hole;
    a test tube having a closed bottom, a top of said test tube and cylindrical side walls extending from said closed bottom to said top of said test tube;
    a cap disposed on said top of said test tube, said cap having a male luer fitting protruding distal from said cap, a hinge and a flip lid hingedly connected to said cap by said hinge, said flip lid further including a connector for releasably locking into said depression to releasably secure said test tube during collection; and
    an open port protruding out from said bottom surface and in fluid communication with said hole, said open port having an interior luer fitting for releasably locking said male luer fitting of said cap into said port and for enabling said test tube to fill only when said container is tilted, said port further including a segmented annual sheath and one of said side walls defining a recessed receptacle detail, said annular sheath protruding from said bottom surface creating a space such that said hinge releasably locks into said space and said flip lid releasably locks into said receptacle detail; and
    a flat adjacent to said open port for supporting said flip lid during collection;
    a finger pad horizontally mounted onto said side walls adjacent to said hole for holding said container;
    said finger pad having a curved portion vertically and distally mounted thereto for slip resistant holding; and
    a vertical support platform attached to at least one of said side walls; a horizontal support platform centrally attached to said vertical support platform and said side walls for flat surface support, said vertical and horizontal support platforms attached opposite said finger pad.

4. A method of filling multiple test tubes with a specimen sample, using a medical device for fluid collection, comprising the steps of:

providing a container having a curved bottom, and open top, and a plurality of side walls therebetween, said bottom having a sloped top surface and a bottom surface, said top surface defining a hole, said container further including an open port protruding out form said bottom surface and in fluid communication with said hole, and a finger pad mounted horizontally on said side walls adjacent to said hole and opposite a vertical and a horizontal support platforms attached to said side walls for flat surface support;

attaching the test tube to said open port by releasably locking said test tube on said open port by an attachment portion, a segmented annular sheath, a depression and a recessed receptacle detail on said container;

collecting a specimen sample in said container and preventing contamination of said specimen by holding said finger pad;

holding said container by said vertical support platform;

tilting said container toward said hole to fill the test tube through said open port;

removing the test tube by placing said horizontal support platform of said container on a flat surface and pulling the test tube out of said open port;

replacing the test tube on said open port with another test tube and tilting said container by said vertical platform toward said hole to fill the other test tube.

* * * * *